(12) United States Patent
Huang et al.

(10) Patent No.: US 7,902,322 B2
(45) Date of Patent: Mar. 8, 2011

(54) NONLINEAR OPTICAL CHROMOPHORES WITH STABILIZING SUBSTITUENT AND ELECTRO-OPTIC DEVICES

(76) Inventors: Diyun Huang, Bothell, WA (US);
Baoquan Chen, Bothell, WA (US)

( * ) Notice: Subject to any disclaimer, the term of this patent is extended or adjusted under 35 U.S.C. 154(b) by 0 days.

(21) Appl. No.: 12/270,714

(22) Filed: Nov. 13, 2008

(65) Prior Publication Data
US 2009/0137772 A1    May 28, 2009

Related U.S. Application Data

(60) Provisional application No. 61/003,443, filed on Nov. 15, 2007.

(51) Int. Cl.
*C08G 75/00* (2006.01)
(52) U.S. Cl. ............ 528/380; 528/422; 549/50; 549/474
(58) Field of Classification Search ................ 528/380, 528/422; 549/50, 474
See application file for complete search history.

(56) References Cited

U.S. PATENT DOCUMENTS

| | | | |
|---|---|---|---|
| 6,361,717 B1 * | 3/2002 | Dalton et al. ................. | 252/582 |
| 6,716,995 B2 | 4/2004 | Huang et al. | |
| 7,078,542 B2 | 7/2006 | Jen et al. | |
| 2008/0009620 A1 | 1/2008 | Goetz et al. | |

FOREIGN PATENT DOCUMENTS

| | | |
|---|---|---|
| JP | 2006-182934 | 7/1994 |
| JP | 2000-256320 | 9/2000 |
| JP | 2002-319234 | 11/2000 |
| JP | 2004-0506630 | 3/2004 |
| WO | WO98-21198 | 5/1998 |

OTHER PUBLICATIONS

Sullivan et al. (JACS, 2007, 129, 7523-7530).*
R. Gujadhur et al., "Formation of aryl-nitrogen bonds using a soluble copper (I) catalyst", Department of Chemistry, Tetrahedron Letters 42 (2001) pp. 4791-4793.
M. Beller et al., "Synthesis of 2,3-Dihydroindoles, Indoles, and Anilines by Transition Metal-Free Amination of Aryl Chlorides", American Chemical Society (2001), vol. 66, No. 4, pp. 1403-1412.
G. Grasa et al., "Amination Reactions of Aryl Halides with Nitrogen-Containing Reagents Mediated by Palladium/Imidazolium Salty Systems", American Chemical Society (2001), vol. 66 No. 23, pp. 7729-7737.
Transmittal of PCT International Search Report for PCT International Application No. PCT/US2008/083418; Sep. 25, 2009.
PCT International Search Report for PCT International Application No. PCT/US2008/083418; Sep. 25, 2009.
PCT Written Opinion of the International Searching Authority for PCT International Application No. PCT/US2008/083418; Sep. 25, 2009.

* cited by examiner

*Primary Examiner* — Randy Gulakowski
*Assistant Examiner* — Shane Fang
(74) *Attorney, Agent, or Firm* — Christopher A. Wiklof; Graybeal Jackson LLP

(57) ABSTRACT

According to an embodiment, a nonlinear optical chromophore includes the structure D-π-A, wherein D is a donor, π is a π-bridge, and A is an acceptor, and wherein at least one of D, π, or A is covalently attached to a substituent group including a substituent center that is directly bonded to at least three aryl groups.

25 Claims, 3 Drawing Sheets

; or

NONLINEAR OPTICAL CHROMOPHORES WITH STABILIZING SUBSTITUENT AND ELECTRO-OPTIC DEVICES

CROSS-REFERENCE TO RELATED APPLICATIONS

This application claims priority benefit under 35 U.S.C. §119(e) from, and to the extent not inconsistent with this application, incorporates by reference herein U.S. Provisional Patent Application Ser. No. 61/003,443; filed Nov. 15, 2007; entitled "NONLINEAR OPTICAL CHROMOPHORES WITH STABILIZING SUBSTITUENT AND ELECTRO-OPTIC DEVICES"; invented by Baoquan Chen & Diyun Huang.

STATEMENT REGARDING FEDERALLY SPONSORED RESEARCH OR DEVELOPMENT

The inventions disclosed herein were made the U.S. Government support pursuant to NRO Contract No. NRO000-07-C-0123 and DARPA Contract No. W31 P4Q-08-C-0198. Accordingly, the Government may have certain rights in the inventions disclosed herein.

BACKGROUND

Nonlinear optical chromophores provide the electro-optic activity in poled, electro-optic polymer devices. Electro-optic polymers have been investigated for many years as an alternative to inorganic materials such as lithium niobate in electro-optic devices. Electro-optic devices may include, for example, external modulators for telecom, RF photonics, and optical interconnects. High electro-optic activity and the stability of electro-optic activity, which is also referred to as "temporal stability", are important for commercially viable devices. Electro-optic activity may be increased in electro-optic polymers by increasing the concentration of nonlinear optical chromophores. However, some techniques for increasing chromophore concentration may decrease temporal stability.

OVERVIEW

According to an embodiment, an organic chromophore includes aryl substituents. The aryl substituents may provide additional steric bulk to the chromophores and allow higher concentrations of the chromophores. The aryl substituents may also provide thermal, temporal, and/or other stability enhancements.

One embodiment is a nonlinear optical chromophore having the structure D-π-A, wherein D is a donor, π is a π-bridge, and A is an acceptor, and wherein at least one of D, π, or A is covalently attached to a substituent group including a substituent center that is directly bonded to at least three aryl groups. In another embodiment, the substituent group includes the structure:

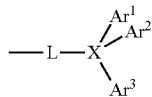

wherein X is the substituent center; $Ar^1$, $Ar^2$, and $Ar^3$ are aryl groups; and L is a covalent linker attached to D, π, or A. According to embodiments, X may be carbon or silicon.

In another embodiment, D has the structure

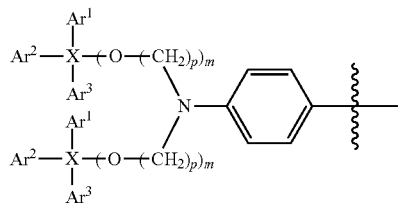

wherein X is a substituent center; $Ar^1$, $Ar^2$, and $Ar^3$ are aryl groups; p is 2-6; and m is 1-3.

Electro-optic polymers including these nonlinear optical chromophores show high electro-optic coefficient. The temporal stability is significantly increased compared to electro-optic polymers including chromophores where alkyl groups are substituted for the aryl groups. The aryl groups may be sterically larger than the alkyl groups.

Another embodiment is an electro-optic polymer including a nonlinear optical chromophore having the structure D-π-A, wherein D is a donor, π is a π-bridge, A is an acceptor, and at least one of D, π, or A is covalently attached to a substituent group including a substituent center that is directly bonded to an aryl group, and wherein the electro-optic polymer has greater temporal stability than when an alkyl group is substituted for the aryl group. According to embodiments, a plurality of aryl groups may be directly bonded to the substituent center.

Another embodiment is a method, including a) providing a polymer including a nonlinear optical chromophore having the structure D-π-A, wherein D is a donor, π is a π-bridge, A is an acceptor, and at least one of D, π, or A is covalently attached to a substituent group including a substituent center that is directly bonded to at least one aryl group; and b) poling the polymer to form and electro-optic polymer, wherein the electro-optic polymer has greater temporal stability than when an alkyl group is substituted for the aryl group.

Other embodiments include electro-optic devices including the nonlinear optical chromophores and electro-optic polymers.

DETAILED DESCRIPTION

Figure 1:
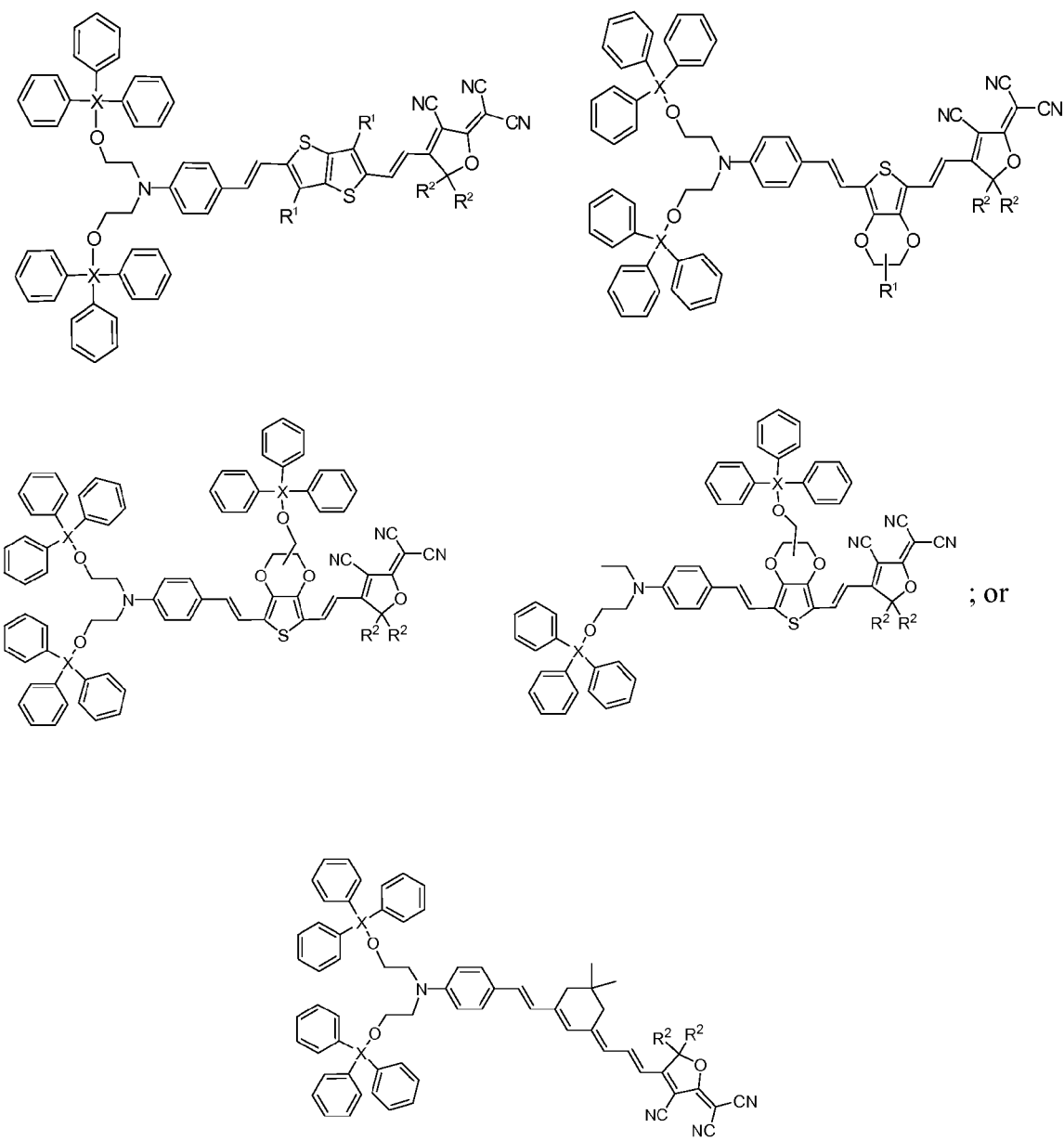
FIG. 1 illustrates nonlinear optical chromophores according to embodiments.

One embodiment is a second order nonlinear optical chromophore having the structure D-π-A, wherein D is a donor, π is a π-bridge, and A is an acceptor, and wherein at least one of D, π, or A is covalently attached to a substituent group including a substituent center that is directly bonded to at least three aryl groups. What is meant by terms such as donor, π-bridge, and acceptor; and general synthetic methods for forming D-π-A chromophores are known in the art, see for example U.S. Pat. No. 6,716,995, incorporated by reference herein.

A donor (represented in chemical structures by "D" or "D'''" where n is an integer) includes an atom or group of atoms that has a low oxidation potential, wherein the atom or group of atoms can donate electrons to an acceptor "A"

through a π-bridge. The donor (D) has a lower electron affinity that does the acceptor (A), so that, at least in the absence of an external electric field, the chromophore is generally polarized, with relatively less electron density on the donor (D). Typically, a donor group contains at least one heteroatom that has a lone pair of electrons capable of being in conjugation with the p-orbitals of an atom directly attached to the heteroatom such that a resonance structure can be drawn that moves the lone pair of electrons into a bond with the p-orbital of the atom directly attached to the heteroatom to formally increase the multiplicity of the bond between the heteroatom and the atom directly attached to the heteroatom (i.e., a single bond is formally converted to double bond, or a double bond is formally converted to a triple bond) so that the heteroatom gains formal positive charge. The p-orbitals of the atom directly attached to the heteroatom may be vacant or part of a multiple bond to another atom other than the heteroatom. The heteroatom may be a substituent of an atom that has pi bonds or may be in a heterocyclic ring. Exemplary donor groups include but are not limited to $R_2N$— and, $RX^1$—, where R is alkyl, aryl or heteroaryl, $X^1$ is O, S, Se, or Te, and n is 1 or 2. The total number of heteroatoms and carbons in a donor group may be about 30, and the donor group may be substituted further with alkyl, aryl, or heteroaryl. The "donor" and "acceptor" terminology is well known and understood in the art. See, e.g., U.S. Pat. Nos. 5,670,091, 5,679,763, and 6,090,332.

An acceptor (represented in chemical structures by "A" or "An" where n is an integer) is an atom or group of atoms that has a low reduction potential, wherein the atom or group of atoms can accept electrons from a donor through a π-bridge. The acceptor (A) has a higher electron affinity that does the donor (D), so that, at least in the absence of an external electric field, the chromophore is generally polarized, with relatively more electron density on the acceptor (D). Typically, an acceptor group contains at least one electronegative heteroatom that is part of a pi bond (a double or triple bond) such that a resonance structure can be drawn that moves the electron pair of the pi bond to the heteroatom and concomitantly decreases the multiplicity of the pi bond (i.e., a double bond is formally converted to single bond or a triple bond is formally converted to a double bond) so that the heteroatom gains formal negative charge. The heteroatom may be part of a heterocyclic ring. Exemplary acceptor groups include but are not limited to —$NO_2$, —CN, —CHO, COR, $CO_2R$, —PO$(OR)_3$, —SOR, —$SO_2R$, and —$SO_3R$ where R is alkyl, aryl, or heteroaryl. The total number of heteroatoms and carbons in a acceptor group is about 30, and the acceptor group may be substituted further with alkyl, aryl, and/or heteroaryl. The "donor" and "acceptor" terminology is well known and understood in the art. See, e.g., U.S. Pat. Nos. 5,670,091, 5,679,763, and 6,090,332.

A "π-bridge" or "electronically conjugated bridge" (represented in chemical structures by "π" or "π′″" where n is an integer) includes an atom or group of atoms through which electrons may be delocalized from an electron donor (defined above) to an electron acceptor (defined above) through the orbitals of atoms in the bridge. Such groups are very well known in the art. Typically, the orbitals will be p-orbitals on double ($sp^2$) or triple (sp) bonded carbon atoms such as those found in alkenes, alkynes, neutral or charged aromatic rings, and neutral or charged heteroaromatic ring systems. Additionally, the orbitals may be p-orbitals on atoms such as boron or nitrogen. Additionally, the orbitals may be p, d or f organometallic orbitals or hybrid organometallic orbitals. The atoms of the bridge that contain the orbitals through which the electrons are delocalized are referred to here as the "critical atoms." The number of critical atoms in a bridge may be a number from 1 to about 30. The critical atoms may be substituted with an organic or inorganic group. The substituent may be selected with a view to improving the solubility of the chromophore in a polymer matrix, to enhancing the stability of the chromophore, or for other purpose.

The substituent group (or any of multiple substituent groups) may be covalently attached to one or more of D, π, and A through a variety of linkages including single bonds, single atoms, heteroatoms, metal atoms (e.g., organometallics), aliphatic chains, aryl rings, functional groups, or combinations thereof. The substituent center may have multiple atoms (e.g., an aryl or aliphatic ring), may be a single atom (e.g., a carbon, silicon, or metal atom), or may be a combination thereof (e.g., a ring system where one aryl group is bonded to one atom of the ring system and the other two aryl groups are bonded to another atom in the ring system).

For example, in some embodiments the substituent center includes a carbon atom, a heteroatom, or a metal atom. In other embodiments, the substituent center may be a carbon atom, a silicon atom, a tin atom, a sulfur atom, a nitrogen atom, or a phosphorous atom. In an embodiment, the substituent center may be a phenyl group.

The aryl groups bonded to the substituent center may be further substituted with alkyl groups, heteroatoms, aryl groups, or a combination thereof. For example, in some embodiments, the aryl groups may, independently at each position, comprise a phenyl ring, a naphthyl ring, a biphenyl group, a pyridyl ring, a bipyridyl group, or an anthracenyl group.

In an embodiment, the substituent group includes the structure:

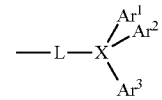

wherein: X is the substituent center; $Ar^1$, $Ar^2$, and $Ar^3$ are the aryl groups; and L is a covalent linker attached to D, π, or A. According to various embodiments, X may be C, Si, Sn, S, N, or P; $Ar^1$, $Ar^2$, and $Ar^3$ each independently include a phenyl ring, a naphthyl ring, a biphenyl group, a pyridyl ring, a bipyridyl group, or an anthracenyl group; and L includes the structure:

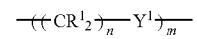

wherein: $R^1$ is independently at each occurrence an H, an alkyl group, or a halogen; $Y^1$ is —$C(R^1)_2$—, O, S, —$N(R^1)$—, —$N(R^1)C(O)$—, —$C(O)_2$—, —$C_6H_6$—, or —$OC_6H_6$—; n is 0-6; and m is 1-3. Donors, acceptors, and π-bridge moieties may include functional groups that may be covalently bonded to the L group.

According to embodiments, D includes:

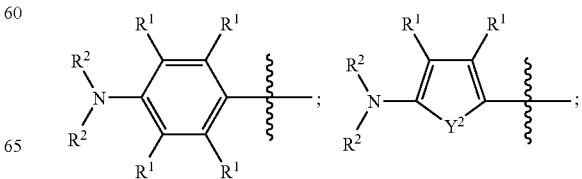

-continued

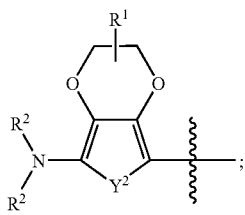

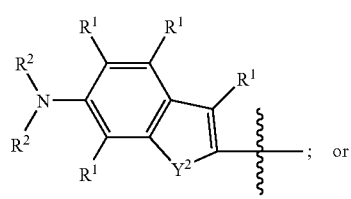; or

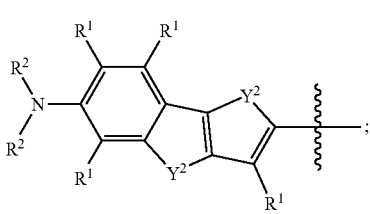;

π includes:

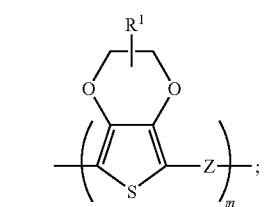 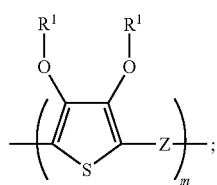

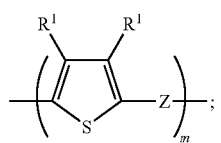 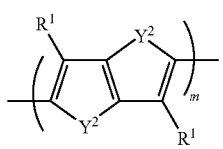

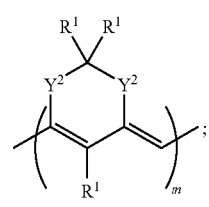; 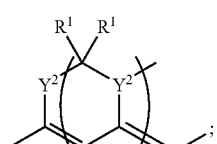;

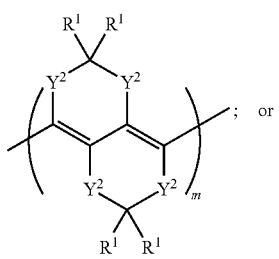; or 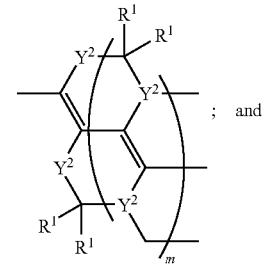; and

A includes:

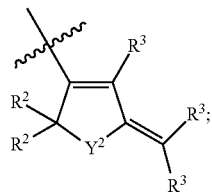

wherein: $R^1$, independently at each occurrence is H, an aliphatic group such as an alkyl or alkoxyl group, or an aryl group. $R^2$, independently at each occurrence, is an alkyl group or an aryl group; Z is a single bond or —CH=CH—; $Y^2$, independently at each occurrence, is C, O, S, $N(R^1)$, or —$C(R^1)_2$—; $R^3$ independently at each occurrence is a cyano group, a nitro group, an ester group, or a halogen; and at least one $R^1$, $R^2$, or $R^3$ includes the substituent group.

In an embodiment, D is

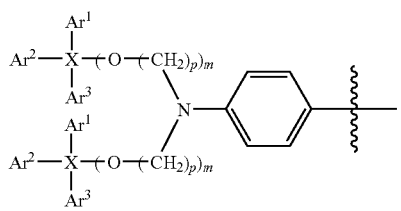

wherein: X is the substituent center; $Ar^1$, $Ar^2$, and $Ar^3$ are aryl groups; p is 2-6; and m=1-3. According to embodiments, X is C or Si.

In an embodiment, π includes:

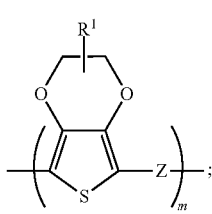 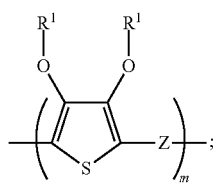

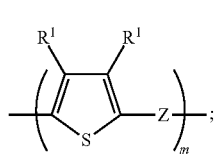; 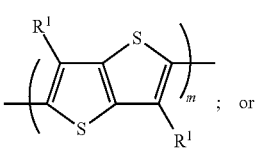; or

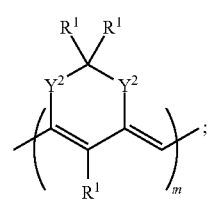;

and A is:

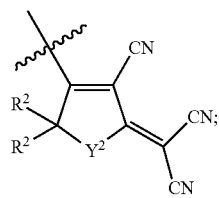

wherein: $R^1$ is independently at each occurrence an H, an alkyl group, or a halogen; Z is a single bond or —CH=CH—; $Y^2$ is O, S, —C($R^1$)$_2$—; $R^2$ is independently at each occurrence an alkyl group or an aryl group; and m=1-3. In embodiments, the nonlinear optical chromophore includes one of the structures shown in FIG. 1 wherein X, $R^1$, and $R^2$ may be as described above. According to an embodiment, a nonlinear optical chromophore has the structure D-π-A, wherein D is a donor, π is a π-bridge, and A is an acceptor; and wherein at least one of D, π, or A is covalently attached to a substituent group including at least one of:

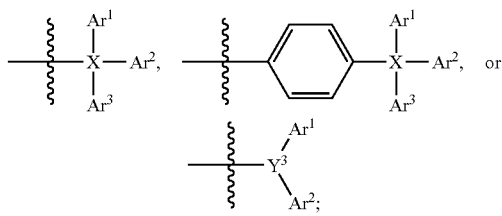

and wherein: X is C or Si; $Y^1$ is —C($R^1$)$_2$—, O, S, —N($R^1$)—, —N($R^1$)C(O)—, —C(O)$_2$—; $Y^3$ is N or P; and $Ar^1$, $Ar^2$, and $Ar^3$ are aryl groups. The aryl groups, D, π, and A may be, as described above for example.

Other embodiments include electro-optic composites and polymers including one or more of the nonlinear optical chromophores described above. Typically, the polymer is poled with an electric field to induce electro-optic activity. Other techniques such as self-organization or photo-induced poling may also be used. The nonlinear optical chromophore may be covalently attached to the polymer matrix (e.g., as in a side-chain polymer or a crosslinked polymer) or may be present as a guest in a polymer matrix host (e.g., a composite material). The nonlinear chromophore may also be present as guest in the polymer matrix and then be covalently bonded or crosslinked to the matrix before, during, or after poling. Polymers that may be used as a matrix include, for example, polycarbonates, poly(arylene ether)s, polysulfones, polyimides, polyesters, polyacrylates, and copolymers thereof.

According to an embodiment, an electro-optic polymer includes a nonlinear optical chromophore having the structure D-π-A, wherein D is a donor, π is a π-bridge, A is an acceptor, and at least one of D, π, or A is covalently attached to a substituent group including a substituent center X that is directly bonded to an aryl group, and wherein the electro-optic polymer has greater temporal stability than when an alkyl group is substituted for the aryl group. The electro-optic polymer may be a side-chain, crosslinked, or composite material. According to an embodiment, the substituent center X is bonded to at least three aryl groups, and the electro-optic polymer has greater temporal stability than when alkyl groups independently are substituted for the aryl groups.

According to an embodiment, the electro-optic composite has greater than 90% temporal stability at 85° C. after 100 hours.

Other embodiments include various methods for making electro-optic composites, and devices therefrom, where the electro-optic composite includes a chromophore as described above. According to an embodiment, a method includes: a) providing a polymer including a nonlinear optical chromophore having the structure D-π-A, wherein D is a donor, π is a π-bridge, A is an acceptor, and at least one of D, π, or A is covalently attached to a substituent group including a substituent center that is directly bonded to an aryl group; and b) poling the polymer to form and electro-optic polymer, wherein the electro-optic polymer has greater temporal stability than when an alkyl group is substituted for the aryl group.

Typically, an aryl group is sterically larger than an alkyl group. Typically, the polymer may be provided as a film by, for example, spin deposition, dip coating, or screen printing. The thin film may also be modified into device structures by, for example, dry etching, laser ablation, and photochemical bleaching. Alternatively, the polymer may be provided by, for example, molding or hot embossing a polymer melt. The poling may include, for example, contact or corona poling. In another method embodiment, the substituent center is bonded to or substituted with at least three aryl groups, and the electro-optic polymer has greater temporal stability than when alkyl groups independently are substituted for the aryl groups.

In some embodiments, the polymer is a composite. In some method embodiments, the aryl group is sterically larger than the alkyl group. In another method embodiment, the polymer has a $T_g$; the $T_g$ of the polymer is within approximately 5° C. compared to when an alkyl group is substituted for the aryl group, and the temporal stability of the polymer is greater compared to when an alkyl group is substituted for the aryl group.

Other embodiments are electro-optic devices including the nonlinear optical chromophores, electro-optic composites, and electro-optic polymers as described above. The devices may include planar waveguides, free standing thin films, single and multi-mode optical waveguides, and other polymers that are passive (e.g., clad polymers such as acrylates). The devices may also have polymers having combinations of any one of the chromophores and/or with other nonlinear optical chromophores. Additionally, a particular device may have two or more different composites and/or polymers including any one of the chromophores above (e.g., a electro-optic waveguide core polymer having one chromophore with a relatively high refractive index and a clad polymer having either the same chromophore in less concentration or a different chromophore so that the refractive index of the clad is lower). In some embodiments, the electro-optic device includes a Mach-Zehnder interferometer, a Michelson interferometer, a micro-ring resonator, or a directional coupler.

EXAMPLES

Figure 2:
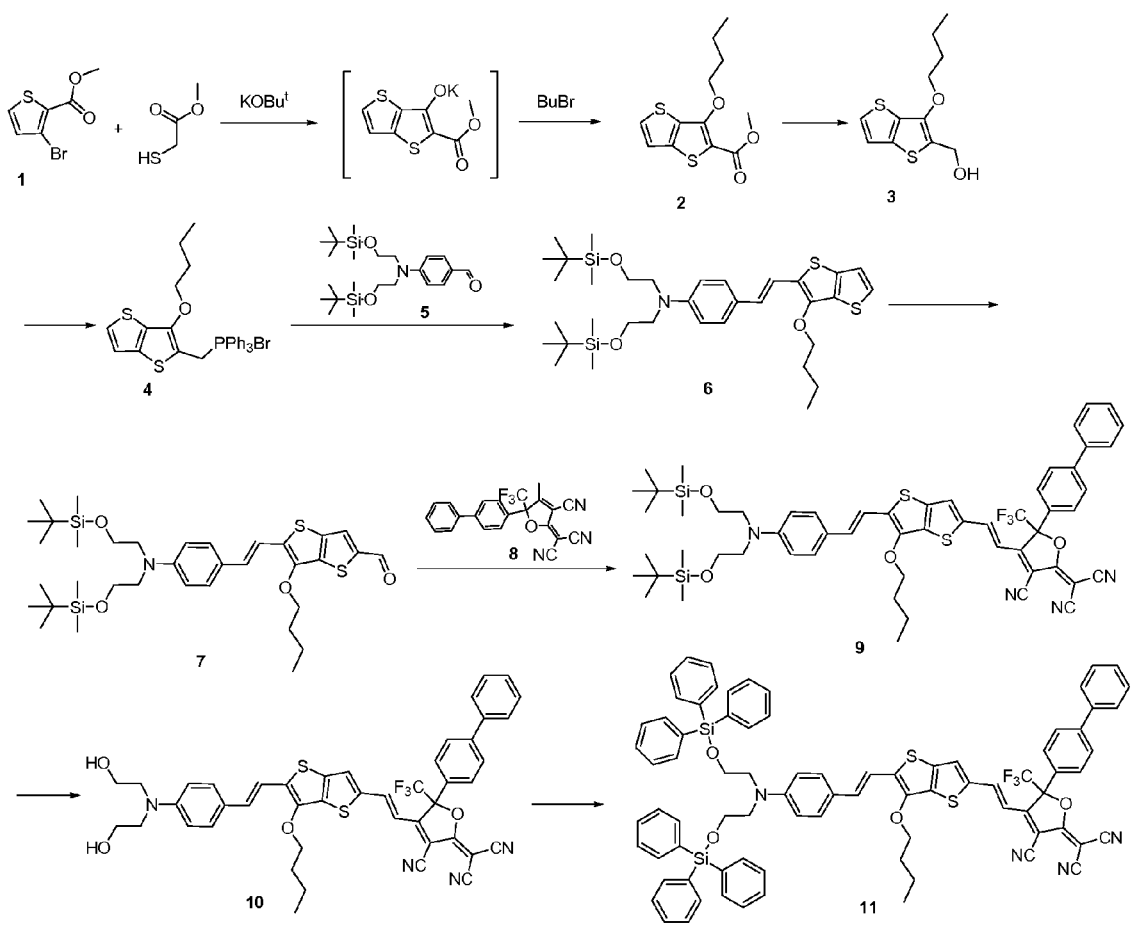
FIG. 2 illustrates the synthesis of a chromophore according to an embodiment.

The following synthetic example refers to FIG. 2.

Compound 2: To compound 1 (10.00 grams) in dioxane (50 ml) in ice bath was added t-BuOK (1M, 55 ml) and Methyl thioglycolate (5.279 grams). The reactants were heated to 80° C. for 2 hours and then to 120° C. for 30 min. Then, most of dioxane was distilled off. 1-Bromobutane (20 ml) and DMSO (80 ml) was added. The reaction was heated to 150° C. for 2 hours. After the reaction was cooled to room temperature, acetic acid in ice water was used to acidify the reaction. The product was extracted with dichloromethane. The dichloromethane layer was separated, dried over MgSO$_4$, filtered, and evaporated to give crude product, which was purified by column chromatography on silica gel to give 10.7 grams of liquid product 2.

Compound 3: Compound 2 (7.72 grams) was dissolved in dry ether under nitrogen. The flask was cooled in dry ice-acetone cooling bath. LiAlH$_4$ (1.08 grams) was added. The cooling bath was removed so that the reaction temperature was brought to room temperature, at which the reaction was kept for 6 hours. The flask was cooled in ice bath. Methanol was added drop-wise to quench the reaction. Brine was added. The organic layer was separated. The aqueous layer was extracted with ether. The combined organic layers were dried over MgSO$_4$, filtered through silica gel packed in funnel. After evaporation, compound 3 was obtained in 4.65 grams.

Compound 4: Compound 3 (4.65 grams) was dissolved in chloroform (100 ml). The flask was cooled in ice bath while triphenylphosphine hydrobromide was added. The reaction was stirred at 0° C. for 30 min, then room temperature for 14 hours, then refluxed for 3 hours. The reaction mixture was precipitated in ether two times to give 8.93 g of product 4.

Compound 6: Compound 4 (6.71 grams) and compound 5 (5.22 grams) were mixed in dry THF (100 ml) under nitrogen and cooled in an ice bath. t-BuOK (1M in THF, 15 ml) was dropped into the mixture via needle. The reaction was stirred at room temperature overnight and quenched with water. The mixture was neutralized with acetic acid. The product was extracted with methylene chloride and purified by flash column using a hexane-methylene chloride mixture to give 3.10 grams of compound 6.

Compound 7: Compound 6 (1.68 grams) was dissolved in dry THF (35 ml) under nitrogen. n-BuLi (2.5M, 1.15 ml) was dropped in via needle at −78° C. The reaction was kept at −30° C. for 70 min. Then, DMF (0.30 ml) was added via needle at −78° C. After 45 min, the reaction was terminated with ice water. The product was extracted with methylene chloride, dried over MgSO$_4$, evaporated, and purified by flash column to give compound 7 (1.32 grams).

Compound 9: Compounds 7 (1.264 grams) and 8 (0.767 grams) (see U.S. Pat. No. 7,078,542 and references therein for preparation of acceptor compounds of this type) were mixed in 10 ml ethanol and 5 ml dry THF under nitrogen. The mixture was heated to 45° C. The reaction was monitored by TLC. When compound 7 disappeared from reaction mixture, the solvent was evaporated on rotary evaporator. The residue was purified by flash column and precipitation of methylene chloride solution in methanol to give 1.03 grams of compound 9 as black powder. U.S. Pat. No. 7,078,542 is incorporated by reference herein.

Compound 10: A total of 5.69 grams of 9 was dissolved in THF (100 ml) under nitrogen. 5 ml of 2N HCl was added. The reaction was stirred at room temperature and monitored by TLC. When the compound 9 disappeared from the reaction mixture, methylene chloride (200 ml) and brine (100 ml) was added. The mixture was neutralized with saturated sodium bicarbonate solution. The organic layer was separated, dried over MgSO$_4$, evaporated, and purified by flash column successively to give 5.69 g of compound 10.

Compound 11: Compound 10 (5.68 grams) was mixed with methylene chloride (50 ml). The flask was cooled in ice bath. triphenylchlorosilane (6.10 grams) and imadazole (1.40 grams) was added successively. The reaction was stirred and monitored by TLC. After about 30 minutes, compound 10 disappeared from the reaction mixture. The salt was filtered out. The product was purified by flash column and precipitation of methylene chloride solution in methanol to give 4.10 grams of compound 11.

Other chromophores were prepared using similar reactions and other starting materials. For example, when X=C, trityl chloride (Ph$_3$C—Cl) may be used in a reaction analogous to that for compound 11.

30 wt % of compound 11 in APC (APC=[biphenyl A carbonate-co-4,4'-(3,3,5-trimethylcyclo-hexylidene)diphenol carbonate], see U.S. Pat. No. 6,750,603) showed very good EO activity of r$_{33}$=81 pm/V and very good temporal stability of 92% retention after 20 hours at 85° C. Temporal stability tests on a Mach-Zehnder modulator showed better than 95% retention of V$_\pi$ after 100 hours at 85° C.

Figure 3:
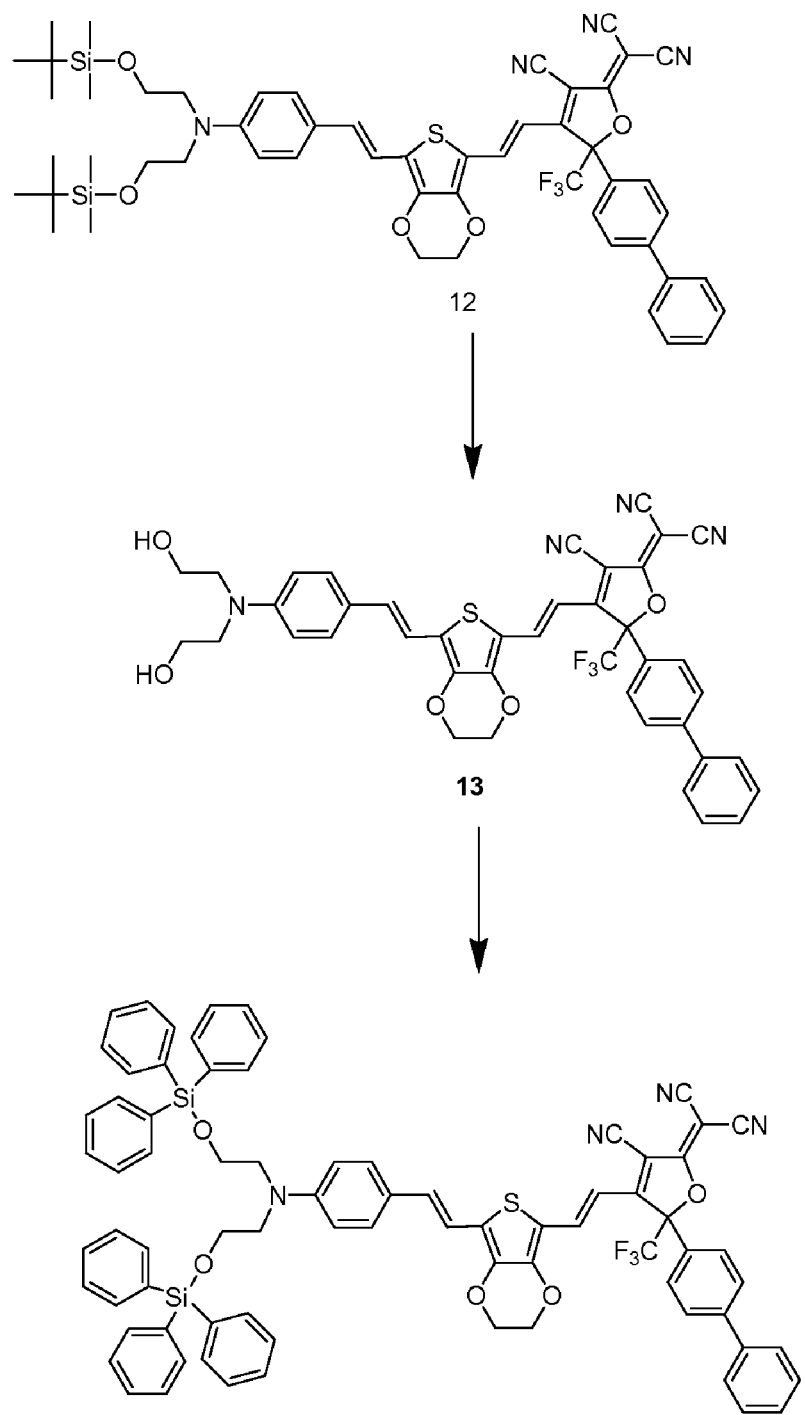
FIG. 3 illustrates the synthesis of a chromophore according to an embodiment.

The following synthetic example refers to FIG. 3.

Compound 13: Compound 12 was dissolved in 70 mL THF while 1N HCl solution (20 mL) was added. It was stirred at room temperature for 2 hours. The mixture was extracted with CH$_2$Cl$_2$, washed with NaHCO$_3$ solution and water, and dried over MgSO$_4$. After evaporating solvent under reduced pressure, it was purified by column chromatography with CH$_2$Cl$_2$/MeOH (5/0.5) as eluting solvents. At total of 1.65 g of compound 13 was obtained in 67% yield.

Compound 14: Compound 13 (0.8 g, 1.07 mmol) and triphenylsilyl chloride (0.945 g, 3.2 mmol) were dissolved in 20 mL of CH$_2$Cl$_2$. After immidazole (0.22 g, 3.2 mmol) was added, the mixture was stirred at room temperature for 1.5 hours. It was then filtered and the solvent was removed under reduced pressure. It was purified by column chromatography to give compound 14 as a solid.

A 50% compound 14 in amorphous polycarbonate (APC) composite had an r$_{33}$ of 90 pm/V, an optical loss of 0.881 dB/cm, a T$_g$ of 140° C., an index of refraction of 1.6711 at 1.55 microns, and a temporal stability in Mach-Zehnder modulators similar to 30% compound 11 in APC as described above. A 24% compound 12 in APC composite, in which the aryl groups are substituted (replaced) with alkyl groups, had an r$_{33}$ of 50 pm/V, an optical loss of 1.44 dB/cm, T$_g$ of 140° C., an index of refraction of 1.6038 at 1.55, and a much lower temporal stability.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A nonlinear optical chromophore comprising:
   the structure D-π-A;
   wherein D is a donor, π is a π-bridge, and A is an acceptor; and
   a substituent group covalently attached to at least one of D, π, or A, and including a substituent center atom directly bonded to at least three aryl groups;
   wherein the substituent center atom lies between the D-π-A structure and the at least three aryl groups.

2. The nonlinear optical chromophore of claim 1; wherein the substituent center is a carbon atom, a silicon atom, or a metal atom.

3. The nonlinear optical chromophore of claim 1; wherein the substituent center is a carbon atom, a silicon atom, a tin atom, a sulfur atom, a nitrogen atom, or a phosphorous atom.

4. The nonlinear optical chromophore of claim 1; wherein the aryl groups independently at each position include at least one selected from the group consisting of a phenyl ring, a naphthyl ring, a biphenyl group, a pyridyl ring, a bipyridyl group, and an anthracenyl group.

5. A nonlinear optical chromophore comprising:
the structure D-π-A;
wherein D is a donor, π is a π-bridge, and A is an acceptor; and
a substituent group covalently attached to at least one of D, π, or A, and including a substituent center atom directly bonded to at least three aryl groups;
wherein the substituent group includes the structure:

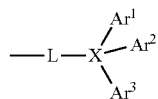

wherein X is the substituent center;
wherein Ar¹, Ar², and Ar³ are the aryl groups; and
wherein L is a covalent linker attached to D, π, or A.

6. The nonlinear optical chromophore of claim 5, wherein:
X is selected from the group consisting of C, Si, Sn, S, N, and P;
wherein Ar³, Ar², and Ar³ each independently include at least one selected from the group consisting of a phenyl ring, a naphthyl ring, a biphenyl group, a pyridyl ring, a bipyridyl group, and an anthracenyl group; and
wherein L includes the structure:

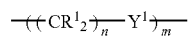

wherein R¹ independently at each occurrence is selected from the group consisting of an H, an alkyl group, and a halogen;
wherein Y¹ independently at each occurrence is selected from the group consisting of —C(R¹)₂—, O, S, —N(R¹)—, —N(R¹)C(O)—, —(O)₂—, —C₆H₆—, and —OC₆H₆—;
wherein n is 0-6; and
wherein m is 1-3.

7. The nonlinear optical chromophore of claim 6, wherein:
D includes the structure

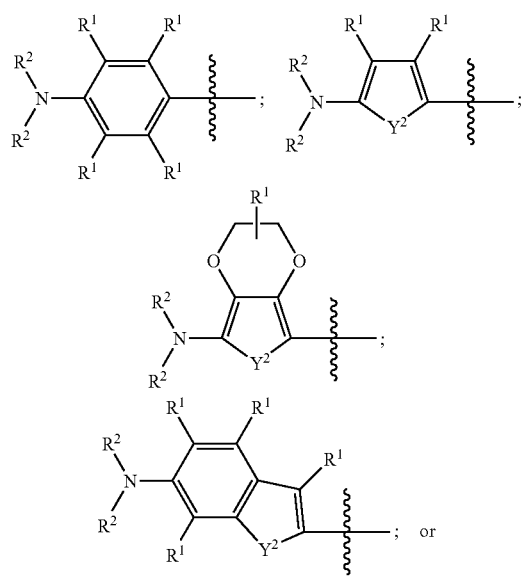

π includes the structure

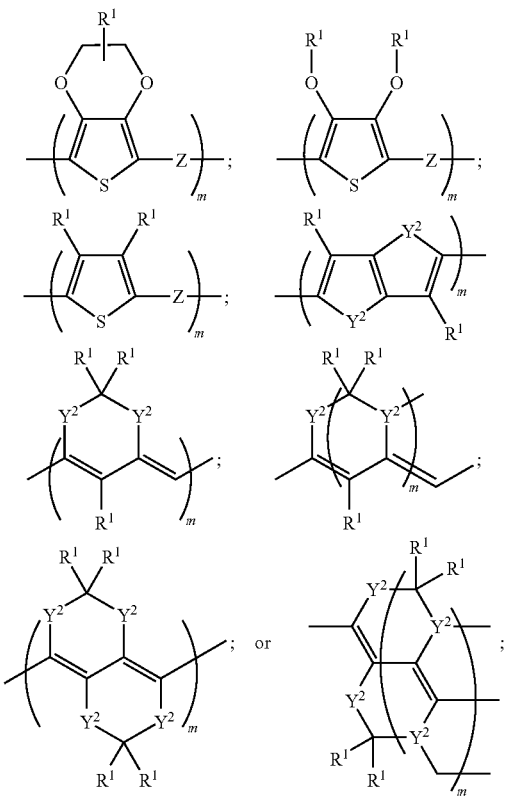

and A includes the structure

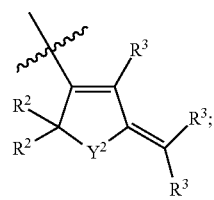

wherein R¹ independently at each occurrence is H, on aliphatic group including alkyl or alkoxyl, or an aryl group;
R² independently at each occurrence is an alkyl group or an aryl group;
Z is a single bond or —CH═CH—;
Y² independently at each occurrence is O, S, N(R¹), or —C(R¹)₂—;
R³ independently at each occurrence is a cyano group, a nitro group, an ester group, or a halogen; and at least one instance of $R^1$, $R^2$, or $R^3$ includes the substituent group.

8. A nonlinear optical chromophore comprising:
the structure D-π-A;
wherein D is a donor, π is a π-bridge, and A is an acceptor; and
a substituent group covalently attached to at least one of D, π, or A, and including a substituent center atom directly bonded to at least three aryl groups;
wherein D is

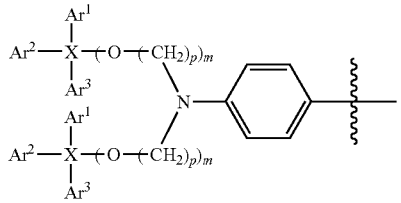

wherein X is the substituent center;
wherein $Ar^1$, $Ar^2$, and $Ar^3$ are the aryl groups;
wherein p is 2-6; and
wherein m=1-3.

9. The nonlinear optical chromophore of claim 8, wherein X is C or Si.

10. The nonlinear optical chromophore of claim 9, wherein π is:

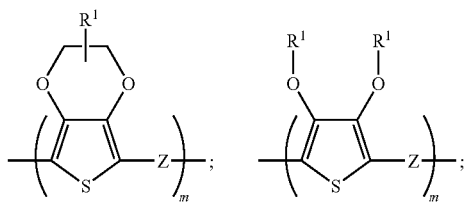

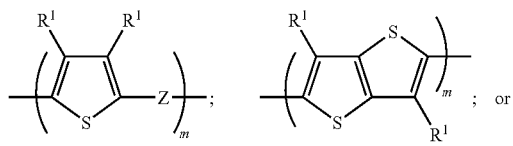

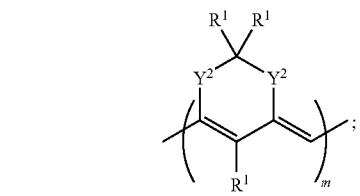

and A is:

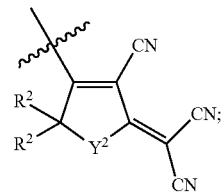

wherein $R^1$ independently at each occurrence is an H, an alkyl group, or a halogen;
wherein Z is a single bond or —CH=CH—;
wherein $Y^2$ is O, S, or —$C(R^1)_2$—;
wherein $R^2$ independently at each occurrence is an alkyl group or an aryl group; and
wherein m=1-3.

11. The nonlinear optical chromophore of claim 10 having the structure

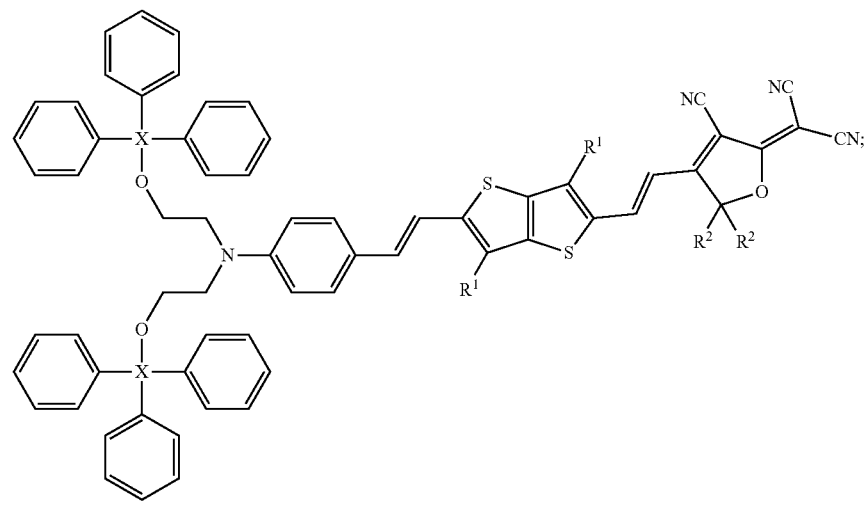

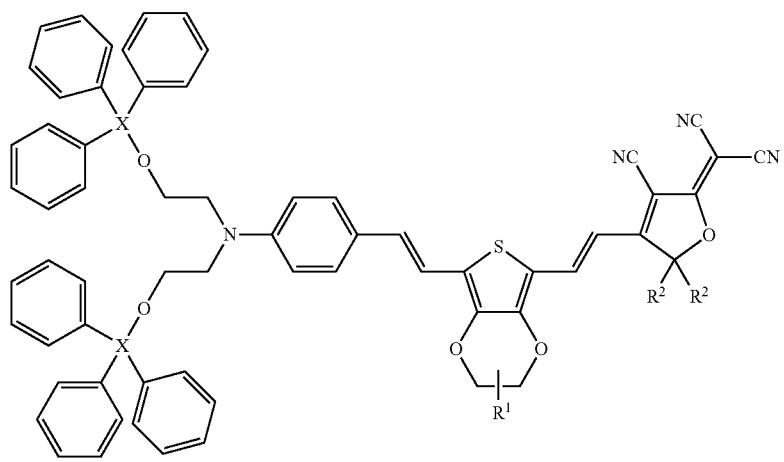
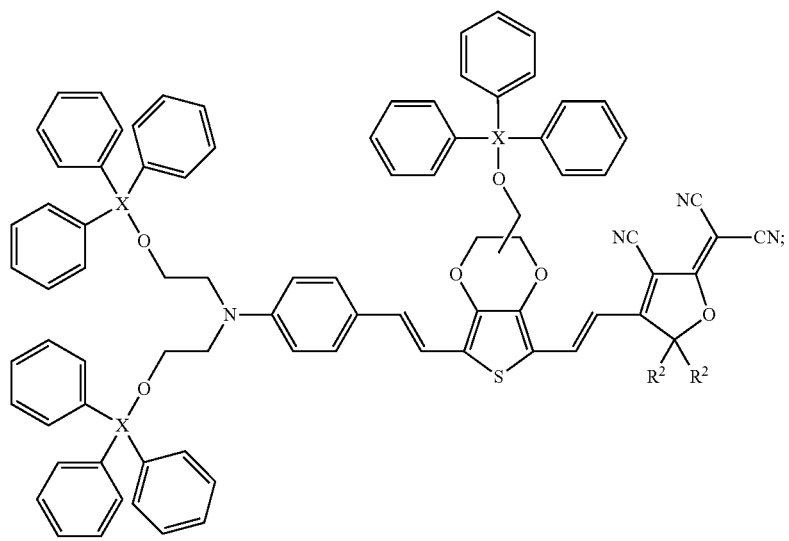
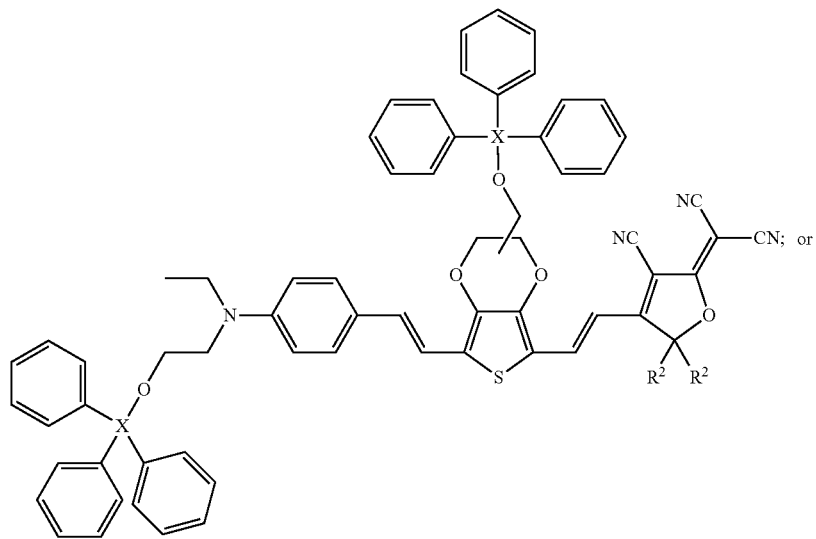

-continued

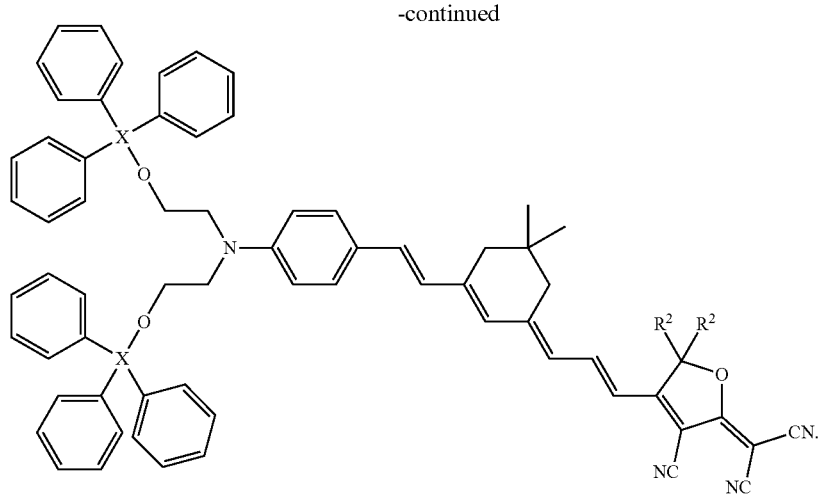

12. A nonlinear optical chromophore, comprising:

the structure D-π-A;

wherein D is a donor, π is a π-bridge, and A is an acceptor, and wherein at least one of D, π, or A is covalently attached to a substituent group including the structure

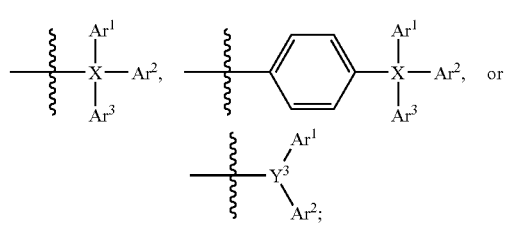

wherein X is C or Si;

wherein $Y^3$ is N or P; and wherein $Ar^1$, $Ar^2$, and $Ar^3$ are aryl groups;

and wherein the substituent group is covalently attached to one nonlinear optical chromophore.

13. The nonlinear optical chromophore of claim 12, wherein the aryl groups independently at each position include a phenyl ring, a naphthyl ring, a biphenyl group, a pyridyl ring, a bipyridyl group, or an anthracenyl group.

14. A nonlinear optical chromophore, comprising:

the structure D-π-A;

wherein D is a donor, π is a π-bridge, and A is an acceptor, and wherein at least one of D, π, or A is covalently attached to a substituent group including the structure

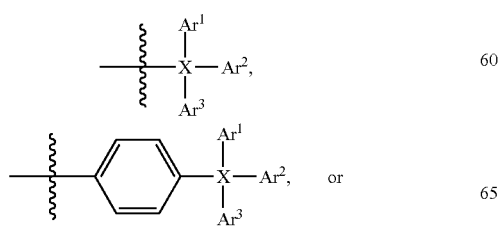

-continued

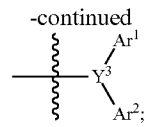

wherein X is C or Si;

wherein $Y^3$ is N or P;

wherein $Ar^1$, $Ar^2$, and $Ar^3$ are aryl groups;

wherein D includes the structure:

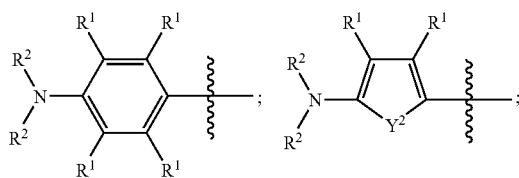

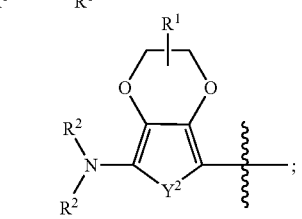

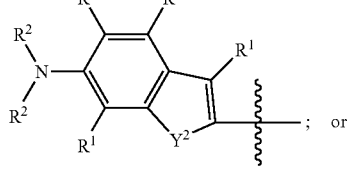

; or

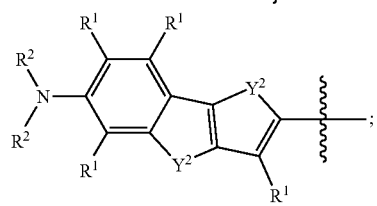

wherein π includes the structure:

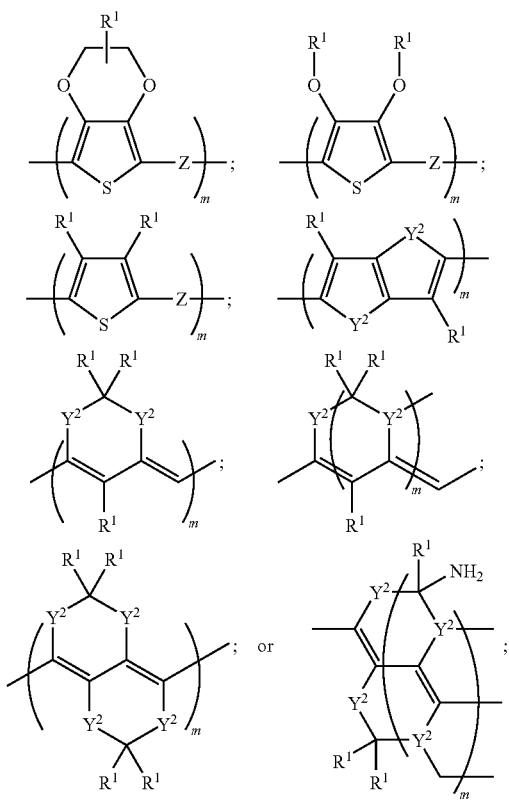

and wherein A includes the structure:

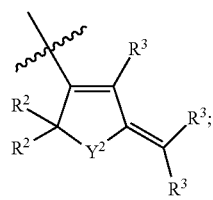

wherein $R^2$ independently at each occurrence is an alkyl group or an aryl group;
wherein Z is a single bond or —CH=CH—;
wherein $Y^2$ independently at each occurrence is O, S, $N(R^1)$, or —$C(R^1)_2$—;
wherein $R^3$ independently at each occurrence is a cyano group, a nitro group, an ester group, or a halogen; and
wherein at least one instance of $R^1$, at least one instance of $R^2$, or at least one instance of $R^3$ includes the substituent group.

15. An electro-optic composite comprising the nonlinear optical chromophore of claim 1, wherein the composite has greater than 90% temporal stability at 85° C. after 100 hours.

16. An electro-optic device comprising:
the nonlinear optical chromophore of claim 1.

17. The electro-optic device of claim 16, wherein the electro-optic device includes a Mach-Zehnder interferometer, a Michelson interferometer, a micro-ring resonator, or a directional coupler.

18. An electro-optic polymer including a nonlinear optical chromophore of any one of claims 1, 5, 8, 12, and 14; and wherein the electro-optic polymer has greater temporal stability than when an alkyl group is substituted for the aryl group.

19. A method, comprising:
a) providing a polymer including a nonlinear optical chromophore of any one of claims 1, 5, 8, 12, and 14; and
b) poling the polymer to form an electro-optic polymer, wherein the electro-optic polymer has greater temporal stability than when an alkyl group is substituted for at least one aryl group.

20. The method of claim 19, wherein the substituent center is substituted with at least three aryl groups; and
wherein the electro-optic polymer has greater temporal stability than when alkyl groups are substituted for the aryl groups.

21. The method of claim 20, wherein the nonlinear optical chromophore includes the structure:

$$—L—X\begin{smallmatrix}Ar^1\\Ar^2\\Ar^3\end{smallmatrix}$$

wherein X is the substituent center;
wherein $Ar^1$, $Ar^2$, and $Ar^3$ are the aryl groups; and
wherein L is a covalent linker attached to D, π, or A.

22. The method of claim 20, wherein the polymer is a composite.

23. The method of claim 20, wherein the aryl group is sterically larger than the alkyl group.

24. The method of claim 20, wherein:
the polymer has a $T_g$;
wherein the $T_g$ of the polymer is within approximately 5° C. compared to when an alkyl group is substituted for the aryl group; and
wherein the temporal stability of the polymer is greater compared to when an alkyl group is substituted for the aryl group.

25. The nonlinear optical chromophore of claim 1; wherein the substituent center is a heteroatom.

* * * * *